United States Patent [19]

Campbell

[11] Patent Number: 5,882,833
[45] Date of Patent: Mar. 16, 1999

[54] TONER RESIN COMPOSITION EMPLOYING A GUANIDINE SALT DERIVATIVE

[75] Inventor: James Stanley Campbell, Manchester, United Kingdom

[73] Assignee: Zeneca Limited, London, England

[21] Appl. No.: 836,487

[22] PCT Filed: Oct. 16, 1995

[86] PCT No.: PCT/GB95/02432

§ 371 Date: May 5, 1997

§ 102(e) Date: May 5, 1997

[87] PCT Pub. No.: WO96/14294

PCT Pub. Date: May 17, 1996

[30] Foreign Application Priority Data

Nov. 3, 1994 [GB] United Kingdom .................. 9422162

[51] Int. Cl.$^6$ .................................................. G03G 9/097
[52] U.S. Cl. ............................................................. 430/110
[58] Field of Search ................................... 430/106, 109, 430/110

[56] References Cited

U.S. PATENT DOCUMENTS 3,776,757  12/1973  Eastman et al. ........................... 430/45
4,663,263   5/1987  Ikeda et al. ............................... 430/110

FOREIGN PATENT DOCUMENTS 178 952  4/1986  European Pat. Off. .
179 642  4/1986  European Pat. Off. .

OTHER PUBLICATIONS

Rasmussen et al: Synthesis, No. 6, 1988, pp. 460–466, see p. 464, entry 51.
Lamattina et al: Journal of Medicinal Chemistry, vol. 33, No. 2, 1990, pp. 643–552, see p. 548; table V see p. 550, compound 130.
Schwobel et al: Liebigs Annalen Der Chemie, 1984, pp. 900–903, see p. 903.
Patent Abstracts of Japan, vol. 10, No. 278 (P–499), Sep. 20, 1986, & JP,A,61 099153 (Canon), May 17, 1986, see abstract.
Patent Abstracts of Japan, vol. 11, No. 112 (P–565), Apr. 9, 1987, & JP,A,61 260255 (Canon) Nov. 18, 1986, see abstract.

*Primary Examiner*—John Goodrow
*Attorney, Agent, or Firm*—Pillsbury Madison & Sutro LLP

[57] ABSTRACT

A toner resin composition comprising a toner resin and an aromatic sulphonic acid salt of a guanidine such as the bis-diphenylguanidine salt of naphthalene-1,5-disulphonic acid. The diphenyl guanidine salts are novel.

9 Claims, No Drawings

TONER RESIN COMPOSITION EMPLOYING A GUANIDINE SALT DERIVATIVE

This application is the national phase of international application PCT/GB95/02432, filed Oct. 16, 1995 which was designated the U.S.

The present invention relates to compositions comprising a toner resin and a guanidine salt of an aromatic sulphonic acid (hereinafter "GAS"), and the use of such salts as a positive charge control agent (hereinafter "CCA"). Some of the salts are novel.

EP 178,952 discloses a composition comprising a base material and a guanidine and its use as a positive CCA in electroreprographic imaging processes.

It has now been found that an aromatic sulphonic acid salt of a guanidine exhibits superior properties as CCA when compared with the guanidine itself especially with respect to superior compatibility with the toner resin, higher triboelectric charge and reduced usage of the guanidine.

According to the present invention there is provided a toner resin composition comprising a toner resin and an aromatic sulphonic acid salt of a guanidine of Formula 1

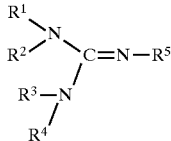

wherein
$R^1$ to $R^5$ are the same or different and are hydrogen, $C_{1-18}$-optionally substituted alkyl, $C_{1-10}$-optionally substituted cycloalkyl, $C_{1-18}$-alkenyl, aralkyl, optionally substituted aryl or heterocyclyl or $R^1$ and $R^2$ together with the nitrogen atom to which they are attached and/or $R^3$ and $R^4$ together with the nitrogen atom to which they are attached, form a 6-membered ring and where at least one of the groups $R^1$ to $R^5$ is other than H.

When $R^1$ to $R^5$ is alkyl or substituted alkyl, the alkyl chain may be linear or branched, but is preferably linear. It is also preferably $C_{1-12}$- and especially $C_{1-6}$-alkyl.

When the alkyl group is substituted, the substituent or substituents are hydroxy, amino, substituted amino, halogen or nitrile.

Preferably, the alkyl group is unsubstituted.

When $R^1$ to $R^5$ is cycloalkyl, it is preferably $C_{3-6}$-cycloalkyl and especially cyclohexyl.

Any substituent present in the cycloalkyl group is preferably $C_{1-4}$-alkyl or $C_{1-4}$-alkoxy, but it is preferred that the cycloalkyl group is unsubstituted.

When $R^1$ to $R^5$ is alkenyl it is preferably $C_{1-10}$-, more preferably $C_{1-6}$- and especially $C_{1-4}$-alkenyl such as propen-2-yl.

When $R^1$ to $R^5$ is aryl it is preferably phenyl or naphthyl which may be substituted by one or more $C_{1-6}$-alkyl, $C_{1-6}$-alkoxy, halogen, nitro or nitrile groups. When present, the substituent is preferably in the 2 and/or 4-position.

When $R^1$ to $R^5$ is heterocyclic, the heterocyclic ring preferably contains 5- or 6-members as in a pyridyl, furanyl or thienyl ring.

When $R^1$ and $R^2$ and/or $R^3$ and $R^4$ together with the nitrogen atom to which they are attached form a 6-membered ring it is preferably morpholino, piperidino, piperazino or N-($C_{1-6}$-alkyl)piperazino.

In the foregoing, halogen means fluorine, bromine, iodine and especially chlorine.

One preferred class of guanidine is where $R^1$ and $R^3$ are the same and $R^2$ and $R^4$ are the same. A particularly preferred class of compound is where $R^1$ and $R^3$ are both hydrogen and $R^2$ and $R^4$ are independently optionally substituted aryl and in an especially preferred class of guanidines, $R^5$ is hydrogen.

Examples of guanidines are diphenylguanidine, triphenylguanidine, tri-1-naphthylguanidine, N,N$^1$-di(4-methyl phenyl) guanidine, N,N'-di(2-methylphenyl) guanidine and N,N$^1$-di(2-methyl-4-ethylphenyl)guanidine.

Good results have been obtained with diphenylguanidine and N,N'-di(2-methylphenyl)guanidine.

The aromatic sulphonic acid (hereinafter "ASA") is preferably carbocyclic and is more preferably a derivative of benzene and especially a derivative of naphthalene. The ASA may contain more than one sulphonic acid group. Preferred ASA's contain two sulphonic acid groups.

The ASA may also contain other substituents such as hydroxy, amino, substituted amino, halogen, nitro or carboxy. Halogen is as hereinbefore defined.

When the ASA contains a substituted amino group, the substituent or substituents are $C_{1-10}$-alkyl and preferably $C_{1-6}$-alkyl which may itself be substituted as described for $R^1$ to $R^5$ hereinbefore.

Examples of suitable ASA's are metanilic, sulphanilic, orthanilic, benzene-1,3-disulphonic, 3-diethylaminobenzene sulphonic, naphthalene-1,5-disulphonic, 6-amino-4-hydroxy-2-naphthalene sulphonic, 1-hydroxy-8-amino-3,6-naphthalene disulphonic, 1-amino-7-naphthalene sulphonic, 1-amino-6-naphthalene sulphonic, 2-naphthylamine-1,5-disulphonic, 2-naphthylamine-1-sulphonic, 2-amino-5-naphthol-7-sulphonic, 1-naphthol-4-sulphonic, 8-amino-1-naphthol-5-sulphonic, 2-naphthylamine-3,6,8-trisulphonic, 4-hydroxy-1-naphthalene sulphonic, 1-naphthol-3,6-disulphonic, 2-naphthol-3,6-disulphonic, 2,6-naphthalene disulphonic, 1,7-dihydroxynaphthalene-3-sulphonic, 4-amino-3-hydroxynaphthalene sulphonic and 4-amino naphthalene sulphonic acids.

It will be appreciated that some of the above ASA's are available as commercial mixtures and hence the ASA may comprise more than the one acid. A typical example of such mixtures is mixed Cleeve's Acid which is 1-amino-6 or 7-naphthalene sulphonic acid.

When the ASA contains more than one sulphonic acid group each of the sulphonic acid groups may form a salt with a guanidine or only one sulphonic acid group may be a salt of a guanidine. When any sulphonic acid group is other than a salt of a guanidine it may be in the form of a free acid or it may be present as the salt of a metal, an amine or a quaternary ammonium compound (hereinafter "QAC"). Preferred metals are alkali metals, especially sodium, potassium and lithium.

Preferred amines or QAC's are those containing $C_{1-24}$-alkyl chains, particularly where the alkyl chain contains more than 6 and especially more than 10 carbon atoms since these amines or QAC's are less volatile and are more resistant to the high temperature employed in the fabrication of toner resin compositions. Examples of amines and QAC cations are dodecylamine, octadecylamine, didecylamine, didocylamine, tetradecylamine, dodecylamine, hexadecylamine, $C_{12-18}$-mixed alkylamines and their N-$C_{1-6}$-alkyl or N,N-di-$C_{1-6}$-alkyl derivatives or N-benzyl derivatives, and particularly their methyl or ethyl derivatives, and N,N-diethyl-N-dodecyl-N-benzylammonium; N,N-dimethyl-N-octadecyl-N-(dimethylbenzyl)ammonium; N,N-dimethyl-N,N-didecyl ammonium; N,N-dimethyl-N,N-didodecylammonium; N,N,N-trimethyl-N-tetradecylammonium; N-benzyl-N,N- dimethyl-N-($C_{12-18}$-alkyl)ammonium; N-(dichlorobenzyl)-N,N-dimethyl-N-dodecylammonium; N-hexadecylpyridinium; N-hexadecyl-N,N,N-trimethylammonium; dodecylpyridinium; N-benzyl-N-dodecyl-N,N-bis(hydroxyethyl)ammonium; N-dodecyl-N-benzyl-N,N-dimethylammonium; N-benzyl-N,N-dimethyl-N-($C_{12-18}$-alkyl)ammonium; N-dodecyl-N,N-dimethyl-N-(1-naphthyimethyl)ammonium and N-hexadecyl-N,N-dimethyl-N-benzylammonium cations.

It is preferred that each sulphonic acid group is present as the salt of a guanidine.

Preferred ASA's contain two sulphonic acid groups and good results have been obtained with the diguanide salt of naphthalene-1,5-disulphonic acid.

The toner resin is a thermoplastic resin suitable for use in the preparation of toner compositions. A preferred toner resin is a styrene or substituted styrene polymer or copolymer such as polystyrene or styrene-butadiene copolymer.

It is especially preferred that the toner resin is a styrene-acrylic copolymer such as a styrene-butyl methacrylate copolymer. Other suitable toner resins are polyesters, especially alkoxylated bis-phenol based polyester resins such as those described in U.S. Pat. No. 5,143,809, polyvinyl acetate, polyalkenes, poly(vinyl chloride), polyurethanes, polyamides, silicones, epoxy resins and phenolic resins. Further examples of these and other resins are given in the book "Electrophotography" by R. M. Shafert (Focal Press): UK 2,090,008, U.S. Pat. No. 4,206,064 and U.S. Pat. No. 4,407,924.

The toner resin composition may contain more than one GAS. The GAS is preferably present in the composition from 0.1 to 12%, more preferably from 0.5 to 10% and especially from 1 to 3% by weight of the total composition.

The toner resin composition may also contain a dyestuff or pigment as colourant.

Thus, according to a further aspect of the invention there is provided a toner resin composition as hereinbefore defined which further comprises a colourant. The colourant is preferably a pigment such as carbon black, magnetite metallised phthalo-cyanine, quinacridone, perylene, benzidine, nigrosine, aniline, quinoline, anthraquinone, azo disperse dye, benzodifuranone, metallised lake or pigment toner or water insoluble salt of a basic dye, including mixtures thereof. The colourant may also be a water soluble basic dye, especially a triphenylmethane dyestuff. The toner composition may contain up to 20% colourant and especially from 3 to 10% relative to the total weight of the toner resin composition.

When the colorant comprises magnetites or a mixture of magnetites and coloured pigment the colourant is preferably present from 5 to 70% and more preferably from 10 to 50% by weight of the toner resin composition. Mixtures of carbon black and magnetite are available commercially and those containing form about 1 to 15% are preferred, especially those containing from 2 to 6% carbon black based on the weight of carbon black and magnetite.

The toner resin composition may be prepared by any method known to the art which typically involves mixing the toner resin with the GAS and optionally the colourant by kneading in a ball mill above the melting point of the resin. Generally, this involves mixing the molten composition for several hours at temperatures from 120° to 200° C., in order to uniformly distribute the GAS and colourant (if present) throughout the toner resin. The toner resin is then cooled, crushed and micronised until the mean diameter of the particles is preferably below $20\mu$ and, for high resolution electroreprography, more preferably from 1 to $10\mu$. The powdered colour toner or toner-resin so obtained may be used directly or may be diluted with an inert solid diluent such as fine silica by mixing for example in a suitable blending machine.

As noted hereinbefore many of GAS's are new. According to a further aspect of the invention there is provided an aromatic sulphonic acid salt of a guanidine of Formula 1.

The GAS may be prepared by any method know to the art and is typically prepared by adding an aqueous acid solution of the guanidine to an aqueous alkaline solution of aromatic sulphonic acid. Preferably, the reaction mix is maintained at a pH above 7 and especially above 9. Generally, there is no need to heat the reactants and the guanidine salt is preferably formed at a temperature from 0° to 40° C., more preferably at a temperature above 10° C., even more preferably above 20° C. and especially below 30° C.

The GAS generally forms a precipitate and is isolated by known techniques such as filtration. Where the GAS does not form a satisfactory precipitate it may be conveniently isolated by evaporation of the water.

As noted hereinbefore, the GAS is suitable as a positive CCA and since most of the salts are white or very pale in colour, the GAS is particularly suited for use in making both coloured and black electroreprographic images.

Thus, as a still further aspect of the invention there is provided the use of an aromatic sulphonic acid of a guanidine of Formula 1 as a CCA.

The invention is further illustrated by the following examples wherein all references are to parts by weight unless indicated to the contrary.

EXAMPLE 1

Preparation of the bis-diphenylguanidine salt of naphthalene-1.5-disulphonic acid Diphenylguanidine (4.22 parts, 0.02M ex AKZO Chemicals) was dissolved in water (50 parts) by adding 4M hydrochloric acid (approx 6.5 ml).

Disodium naphthalene-1,5-disulphonate (3.32 parts, 0.01M, ex FLUKA) was dissolved in water (50 parts) at 20°–25° C. and 0.5M sodium hydroxide solution added to give a pH of between 9 and 10.

The solution of the diphenylguanidine hydrochloride was added whereupon a white precipitate immediately formed. This was filtered off, washed with water and dried.

Yield=6.06 parts (86% theory) mp 297°–298° C. This is GAS 1.

Elemental analysis

Theory 60.8% C, 4.8% H, 11.8% N, 9.0% S

Found 60.7% C, 5.0% H, 11.8% N, 8.7% S

EXAMPLE 2

Preparation of diphenylguanidine salt of 1-naphthol-4-sulphonic acid

This was prepared by a similar manner to the salt described in Example 1 except using diphenylguanidine (10.55 parts, 0.05M) and 1-naphthol-4-sulphonic acid (12.3 parts, 0.05M ex Fluka). The salt was obtained as an off-white solid (11.36 parts). This is GAS 2.

Elemental analysis

Theory 63.4% C, 4.8% H, 9.7% N, 7.4% S

Found 64.3% C, 5.5% H, 11.1% N, 6.3% S

EXAMPLE 3

Preparation of diphenylguanidine salt of 8-amino-1-naphthol-5-sulphonic acid

This was prepared in a similar manner to the salt described in Example 1 except using diphenylguanidine (5.28 parts, 0.025M) and the acid (13.48 parts, 0.025M ex Aldrich). The salt was obtained as a dark solid (10.03 parts) melting at about 158° C. This is GAS 3.

Elemental analysis
Theory 61.3% C, 4.9% H, 12.4% N, 7.1% S
Found 60.1% C, 5.5% H, 11.8% N, 5.9% S

EXAMPLE 4

Preparation of bis(di-o-tolylguanidine) salt of naphthalene-1.5-disulphonic acid This was prepared in a similar manner to the salt described in Example 1 except using di-o-tolylguanidine (11.95 parts, 0.05M ex Vulnax) and acid (8.30 parts, 0.025M ex BDH). The salt was obtained as a pink solid (17.19 parts). This is GAS 4.

Elemental analysis
Theory 62.7% C, 5.5% H, 11.0% N, 8.4% S
Found 62.6% C, 5.7% H, 11.1% N, 8.5% S

EXAMPLE 5

Evaluation as CCA

Styrene-acrylic resin (300 parts, Almacryl B-1500 ex Image Polymers Company) and GAS (7.5 parts) were melt-kneaded at 160°–168° C. for 60 minutes. After cooling, the toner resin was pre-ground in a ball-mill to give a mean particle size of between 100 and 150$\mu$ and then finely ground to give a mean particle size between 5 and 30$\mu$.

The ground toner resin (0.4 parts) was then stirred with an uncoated iron powder carrier (19.6 parts, Type 13 ex Xerox Inc) and the tribo-charge determined using a Toshiba TB 200 "Blow off" apparatus.

The results are given in Table 1 below

TABLE 1

| Agent | M | Tribo-charge after t mins ($\mu$Ccm$^{-1}$) | | | |
|---|---|---|---|---|---|
| | | 2 | 10 | 20 | 30 |
| GAS 1 | 0.59 | 32 | 39 | 46 | 49 |
| GAS 4 | — | — | — | — | 51.95 |
| Control | 1 | 32 | 34 | 38 | 41 |

Footnote to Table 1:

Control contained 7.5 parts of diphenylguanidine and M is the relative amount of diphenylguanidine in the CCA compared with Control (1).

This example illustrates that the guanidine when present as a salt of an aromatic sulphonic acid is superior as a CCA to that where the guanidine alone is present especially when the reduced relative concentration of guanidine is taken into consideration.

I claim:

1. A toner resin composition comprising a toner resin and an aromatic sulphonic acid salt of a guanidine of formula 1

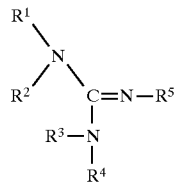

wherein $R^1$ to $R^5$ are the same or different and are hydrogen, $C_{1-18}$-optionally substituted alkyl, $C_{1-10}$-optionally substituted cycloalkyl, $C_{1-18}$-alkylene, aralkyl, optionally substituted aryl or heterocyclyl or $R^1$ and $R^2$ together with the nitrogen atom to which they are attached and/or $R^3$ and $R^4$ together with the nitrogen atom to which they are attached, form a 6-membered ring and where at least one of the groups $R^1$ to $R^5$ is other than hydrogen provided that the aromatic sulphonic acid salt of a guanidine of formula 1 is not $N^1,N^3$-diisopropyl- $N^2,N^2$-dimethylguanidinium-2,4,6-trinitrobenzenesulphonate.

2. A composition as claimed in claim 1 wherein $R^1$ and $R^3$ are the same.

3. A composition as claimed in either claim 1 or claim 2 wherein $R^2$ and $R^4$ are the same.

4. A composition as claimed in any one of claims 1 to 3 wherein $R^5$ is hydrogen.

5. A composition is claimed in any one of claims 1 to 4 wherein the guanidine is diphenylguanidine or N,N'-di-(2-methylphenyl)guanidine.

6. A composition as claimed in any one of claims 1 to 5 wherein the aromatic sulphonic acid is a derivative of naphthalene.

7. A composition as claimed in claim 6 wherein the aromatic sulphonic acid contains two sulphonic acid groups.

8. A composition as claimed in any one of claims 1 to 7 wherein the aromatic sulphonic acid is naphthalene-1,5-disulphonic acid.

9. A composition as claimed in any one of claims 1 to 8 which further comprises a colorant.

* * * * *